(12) United States Patent
Tao et al.

(10) Patent No.: US 10,060,929 B2
(45) Date of Patent: Aug. 28, 2018

(54) DIFFERENCE GEL ELECTROPHORESIS OF PHOSPHOPROTEOME

(71) Applicant: PURDUE RESEARCH FOUNDATION, West Lafayette, IN (US)

(72) Inventors: Weiguo Andy Tao, West Lafayette, IN (US); Linna Wang, West Lafayette, IN (US)

(73) Assignee: PURDUE RESEARCH FOUNDATION, West Lafayette, IN (US)

(*) Notice: Subject to any disclaimer, the term of this patent is extended or adjusted under 35 U.S.C. 154(b) by 0 days.

(21) Appl. No.: 15/004,339

(22) Filed: Jan. 22, 2016

(65) Prior Publication Data

US 2016/0216275 A1    Jul. 28, 2016

Related U.S. Application Data

(60) Provisional application No. 62/106,998, filed on Jan. 23, 2015.

(51) Int. Cl.
| | |
|---|---|
| G01N 33/68 | (2006.01) |
| C07F 7/28 | (2006.01) |
| G01N 33/58 | (2006.01) |
| G01N 31/00 | (2006.01) |
| C07D 231/56 | (2006.01) |
| G01N 21/64 | (2006.01) |
| G01N 27/447 | (2006.01) |
| G01N 21/77 | (2006.01) |
| G01N 1/30 | (2006.01) |

(52) U.S. Cl.
CPC ....... *G01N 33/6842* (2013.01); *C07D 231/56* (2013.01); *C07F 7/28* (2013.01); *G01N 31/00* (2013.01); *G01N 33/582* (2013.01); *G01N 33/683* (2013.01); *G01N 1/30* (2013.01); *G01N 21/6428* (2013.01); *G01N 21/6456* (2013.01); *G01N 27/44726* (2013.01); *G01N 27/44795* (2013.01); *G01N 2021/6421* (2013.01); *G01N 2021/6439* (2013.01); *G01N 2021/7786* (2013.01); *G01N 2440/14* (2013.01); *G01N 2570/00* (2013.01)

(58) Field of Classification Search
CPC ............ G01N 33/6842; G01N 33/582; G01N 21/6428; G01N 27/44743; G01N 27/44747; G01N 27/44795; G01N 2440/14; G01N 2570/00; G01N 2021/6439; C07F 7/28
See application file for complete search history.

(56) References Cited

U.S. PATENT DOCUMENTS

2013/0202536 A1* 8/2013 Mustaev ............ C07D 215/38
424/9.6

* cited by examiner

*Primary Examiner* — Shafiqul Haq
(74) *Attorney, Agent, or Firm* — Purdue Research Foundation; Yonghao Hou

(57) ABSTRACT

A novel imaging reagent and gel-based method for analyzing and comparing phosphoproteomes on the same gel are disclosed herein.

2 Claims, 4 Drawing Sheets

DIFFERENCE GEL ELECTROPHORESIS OF PHOSPHOPROTEOME

CROSS-REFERENCE TO RELATED APPLICATIONS

The present U.S. patent application is related to and claims the priority benefit of U.S. Provisional Patent Application Ser. No. 62/106,998, filed Jan. 23, 2015, the contents of which is hereby incorporated by reference in its entirety into this disclosure.

STATEMENT OF GOVERNMENT INTEREST

This invention was made with government support under GM088317 awarded by the National Institutes of Health. The government has certain rights in the invention.

TECHNICAL FIELD

The present disclosure generally relates to analysis of phosphoproteins, and in particular to specific and differential visualization, identification, and comparison of phosphoproteomes.

BACKGROUND

This section introduces aspects that may help facilitate a better understanding of the disclosure. Accordingly, these statements are to be read in this light and are not to be understood as admissions about what is or is not prior art.

There are numerous current limitations in phosphoproteomic analysis. Large-scale phosphorylation analysis, in particular the quantitative measurement of changes in phosphorylation, is vital to understanding how signaling networks interact and function, and how they are misregulated in disease states. For the past decade, gel-free shotgun sequencing has become the major strategy for in-depth phosphoproteomic analyses. At present, large-scale phosphoproteome experiments frequently require extensive fractionation, phosphopeptide enrichment of each fraction, long LC gradient for individual mass spectrometric analysis, and integration of large datasets. Although thousands or even tens of thousands of protein phosphorylation sites can be identified, many researchers may be only interested in a limited number of phosphoproteins that show response to a signaling event. Therefore, large-scale phosphoproteomics has become time-consuming and cost-prohibitive for a typical project. On the other hand, gel-based proteomic strategy, which often combines protein separation by 1- or 2-dimensional polyacrylamide gel electrophoresis (1D or 2D-PAGE) with protein identification by mass spectrometry (MS), has pioneered the field of proteomics and has remained a workhorse in proteomic studies. Difference Gel Electrophoresis (DIGE) overcomes the poor reproducibility among gel experiments and is widely used to profile whole proteome expression under different conditions. DIGE allows researchers to visualize proteins expressed differentially before choosing relevant ones for identification by mass spectrometry, typically by high speed MALDI-TOF/TOF. The applicability of gel-based proteomic strategy in phosphoproteomics has been largely limited by the lack of technologies for specific and quantitative detection of phosphoproteins in gels. It was proposed to use 32P/33P radioactive labeling for difference phosphoproteomes. However, it is a serious safety concern, needs large amount of radioactive material to label endogenous proteins, and is not compatible with mass spectrometric analyses. There have been several attempts to stain phosphoproteins for large-scale phosphoproteomes in 2D gels, including commercial products such as Pro-Q Diamond and Phos-tag. While these assays show some promise in terms of versatility, they are limited by low specificity of binding between the incorporated metal ions and phosphate groups. Highly abundant non-phosphorylated proteins can also be stained in these studies, making these methods less reliable for large-scale phosphoproteomes. These existing commercial reagents are therefore typically used for staining or mobility assays of simple samples and cannot be utilized for simultaneous detection and quantitation within the same gel. There is therefore an unmet need for a routine and effective analysis of relevant phosphoproteins.

SUMMARY

In one aspect, an imaging reagent is disclosed, which has at least three functional groups, a photo-reactive group, a metal chelating group, and a fluorophore, wherein the fluorophore has a color that is dependent on a number of protein samples. The imaging reagent is configured to bind and introduce a fluorophore onto phosphoproteins.

In another aspect, a method for analyzing and comparing phosphoproteomes on the same gel is presented. The method can include the steps of binding an imaging compound to at least one phosphoprotein, incubating at least two protein samples with two imaging reagents that contain different fluorophores, crosslinking the phosphoproteins via ultraviolet (UV) crosslinking, mixing at least two protein samples to form one mixed protein sample, loading the mixed protein sample onto for isoelectric focusing (IEF), performing sodium dodecyl sulfate polyacrylamide gel electrophoresis (SDS PAGE), and scanning the SDS PAGE with an excitation wavelength for each of a plurality of dyes for comparative visualization. The imaging compound can be a metal ion. The metal ion can be titanium (IV), Zr (IV), Fe (III), and/or Ga (III). The fluorophore can be Cy3 and/or Cy5.

BRIEF DESCRIPTION OF DRAWINGS

FIG. 4a shows a quantitative visualization of phosphoproteins in a five-protein mixture and the overlap of Cy3 and Cy5 excitation scan; proteins in different portions were labeled and then mixed for DiGEP analysis.

FIG. 4b shows a stain by Coomassie blue for the proteins in FIG. 4a.

DETAILED DESCRIPTION

Figure 1:
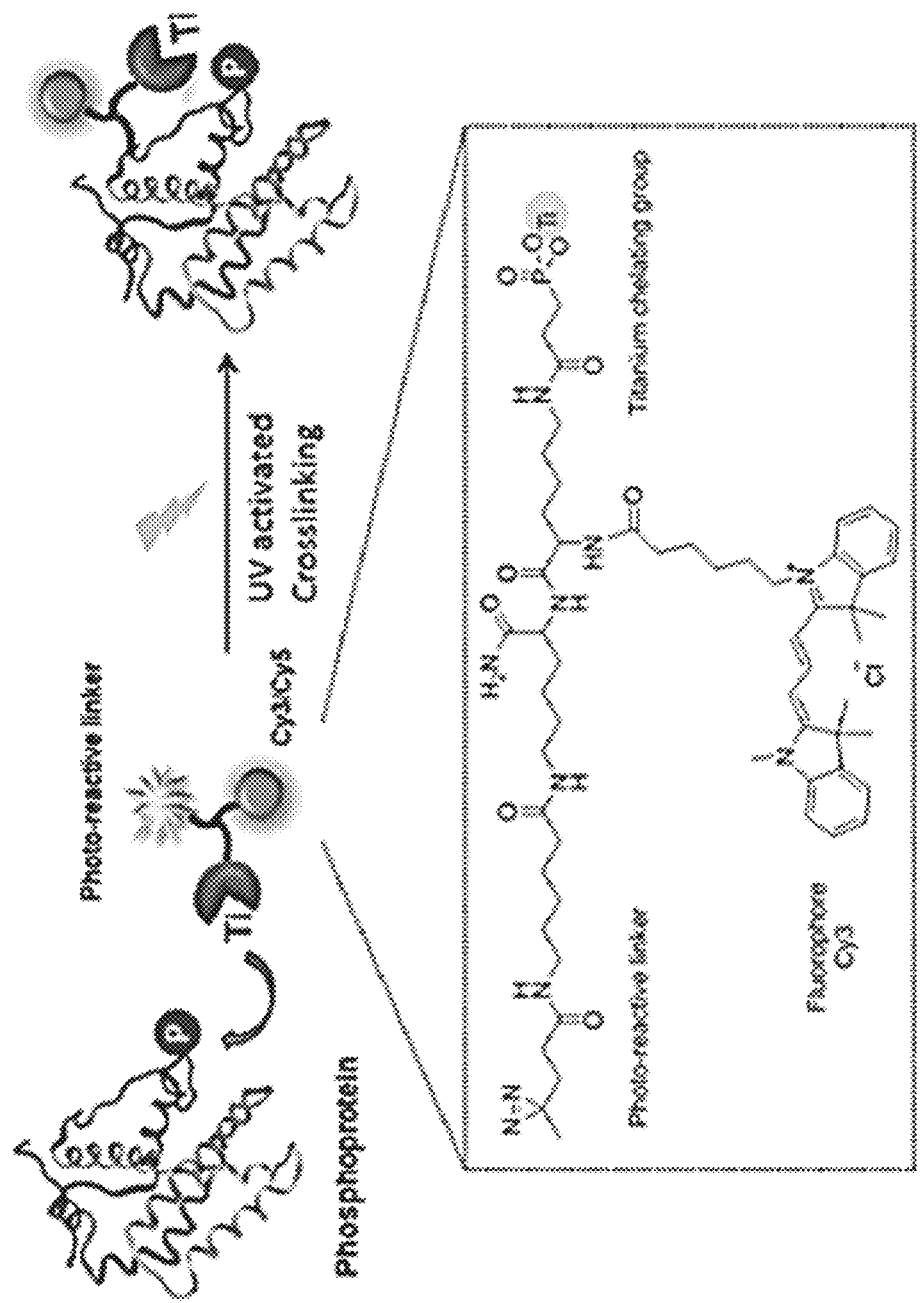
FIG. 1 is an illustration depicting DiGEP imaging reagents to bind and introduce a fluorophore onto phosphoproteins.

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

In response to the unmet need for a novel tool to analyze phosphoproteins, we herein present a novel gel-based method and system. This method and system, termed Differential Gel Electrophoresis of Phosphoproteome (DiGEP) utilizes the high specificity of metal ions (such as Ti (IV), Zr (IV), Fe (III), and Ga (III)) toward phosphate group and introduces fluorophores through covalent crosslinking on all phosphoproteins to achieve difference visualization of phosphoproteomes in gels. We use Ti (IV) as the example in this description for simplicity. Such use is not intended to be limiting. Rather, other metal ions can be used, including but not limited to Zr (IV), Fe (III), and Ga (III).

DiGEP analyses allow us to first visualize phosphoproteins on a single gel and then only choose relevant proteins for in-gel digestion and mass spectrometric analysis. With high specificity, selectivity, and quantitative labeling of phosphoproteins, DiGEP provides researchers with a novel technique for routine phosphorylation assays. Major pIMAGO applications include (but are not limited to) quantitative phosphorylation measurement, in vitro kinase assay, kinase and phosphatase activity assay, kinase/phosphatase inhibitors screening, and detection of in vivo phosphorylation. It is estimated that over 200,000 life sciences laboratories in academia and industries can benefit from such a technology worldwide. In addition, because of its use with the standard fluorophores (Cy3 and Cy5), the DiGEP platform is fully compatible with gel systems and imaging software already developed for Difference Gel Electrophoresis (DIGE).

Applications exist of water-soluble Ti (IV)-based nanopolymers for phosphopeptide enrichment, phosphoprotein detection on microplates, on membrane, and for multiplexed analyses. The herein disclosed DiGEP platform to quantitatively visualize and identify low-abundant phosphorylated proteins in a variety of biological contexts is novel and provides a major technique for large-scale phosphorylation analyses with affordable cost. The innovative features of the herein disclosed technology lie in the creation of small water-soluble and multi-functionalized molecules, capable of specific and strong binding to low-abundant phosphoproteins, and containing secondary functional groups to crosslink phosphoproteins and introduce fluorophores for differential detection.

In one embodiment, the herein disclosed DiGEP technology is presented as scalable and versatile products for phosphoproteomic analyses in a broad range of biological applications. The core of DiGEP is a novel imaging compound functionalized with a titanium (IV) metal ion for very strong and highly selective binding to phosphoproteins, a fluorophore (Cy3 or Cy5), and a photo-reactive linker (the space between the photo-reactive linker and the Ti (IV) ion can be modified as needed to address any issues that may arise relating to decreasing identification of phosphopeptides in proteins such as α-casein and ovalbumin due to covalent crosslinking). (FIG. 1, which is an illustration depicting DiGEP imaging reagents to bind and introduce a fluorophore onto phosphoproteins). Two protein samples are incubated with the imaging reagents bearing Cy3 or Cy5, followed by UV crosslinking. The samples are then mixed and loaded onto isoelectric focusing (IEF) for first dimension and the strip is transferred to an SDS PAGE. After the gel electrophoresis, the gel is scanned with the excitation wavelength for each of the dye separately for comparative visualization. DiGEP allows us to visualize changes in protein phosphorylation between two samples. Reciprocal labeling as an option can be achieved to offset any potential nonspecific background. Similar to DIGE, DiGEP overcomes limitations in traditional 2D electrophoresis due to inter-gel variation, which can be considerable even with identical samples. Because the proteins from the different sample types (e.g. healthy/diseased, virulent/non-virulent) are run on the same gel they can be directly compared. After imaging software identifies the spots with significant changes, in gel digestion can be carried out and phosphopeptides enriched for MALDI-TOF/TOF analyses (FIG. 2, which is a schematic illustration of the herein disclosed DiGEP strategy for phosphoproteomic analyses).

In one embodiment, in order to accomplish the specific, differential phosphoprotein detection in gel (and more specifically, the optimization of the imaging reagents for DiGEP detection), the optimization is focused on improving the sensitivity and selectivity of the technique through reducing background/nonspecific binding and enhancing sensitivity and quantitation of fluorescence signals. This is first achieved through fine-tuning the synthesis of the imaging reagents to find the best combination of Ti (IV) ion, fluorophore, and photo-reactive linker. A variety of spectrometric tools can be utilized for quality control. For example, NMR is used to examine the purity of the compound and ICP-MS is accurate to determine whether each molecule contains one Ti (IV) ion. These steps ensure the consistency of the synthesis. The quality of each synthesized batch is further confirmed using a benchmark phosphoprotein/non-phosphoprotein mixture for consistency. Spectrometric characterization of the imaging reagents is carried out as well.

Figure 3A:
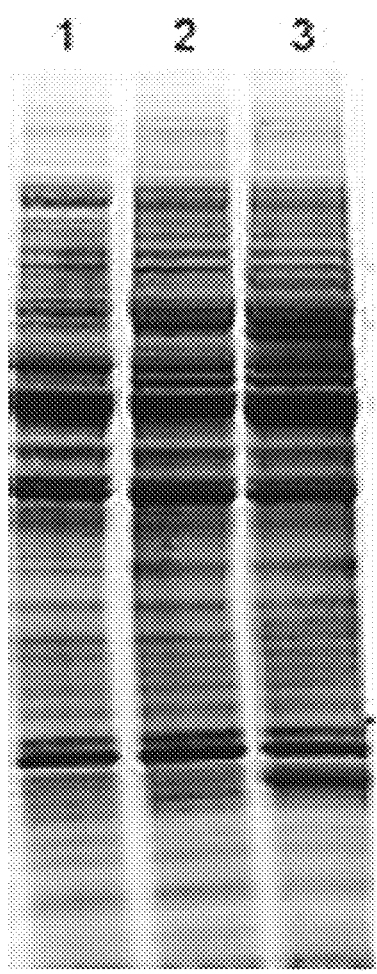
FIG. 3a shows results of studies showing detection of endogenous phosphorylated proteins from E. coli whole cell extract (Lane 1: 25 μg E. coli lysate protein; Lane 2: 25 μg E. coli lysate protein with CIAP; Lane 3: 25 μg E. coli lysate protein treated with CIAP and spiked with 500 ng of five-protein mixture), and further showing protein gel staining with Sypro Ruby indicates equal cell extract loading.
Figure 3B:
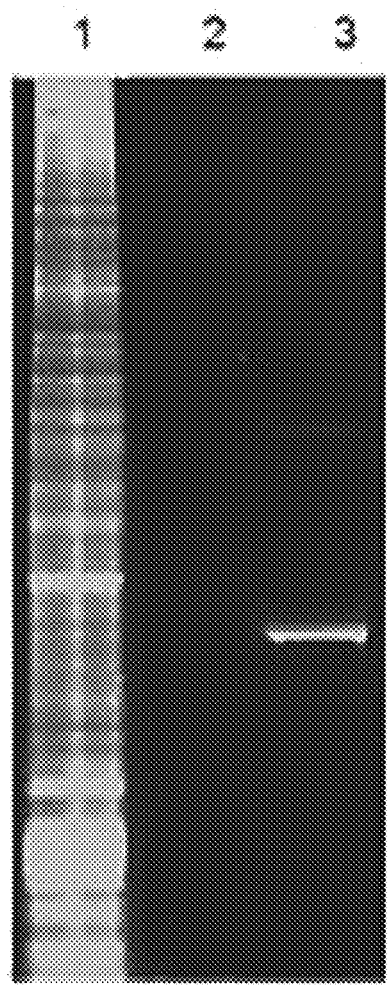
FIG. 3b shows results of studies showing detection of endogenous phosphorylated proteins from E. coli whole cell extract (Lane 1: 25 μg E. coli lysate protein; Lane 2: 25 μg E. coli lysate protein with CIAP; Lane 3: 25 μg E. coli lysate protein treated with CIAP and spiked with 500 ng of five-protein mixture), and further showing that the DiGEP method was able to detect endogenous phosphorylated proteins labeled with one of the imaging reagents in a whole cell extract of E. coli BL21 strain.

In another embodiment, the optimization of the DiGEP procedure is accomplished by testing the appropriate amount of the imaging reagents to be used, staining and washing solutions. Major contaminations come from highly acidic proteins, and these have been successfully eliminated by including different selectivity enhancers, such as glycolic acid, lactic acid, and dihydroxybenzoic acid (DHB), to minimize potential interferences. Protein mixtures containing phosphoproteins and non-phosphoproteins are used to optimize the detection conditions and reach sub-nanogram level of sensitivity. We then use whole cell extracts to evaluate the sensitivity and specificity. FIGS. 3a and 3b represent results of studies showing detection of endogenous phosphorylated proteins from E. coli whole cell extract (Lane 1: 25 μg E. coli lysate protein; Lane 2: 25 μg E. coli lysate protein with CLAP; Lane 3: 25 μg E. coli lysate protein treated with CLAP and spiked with 500 ng of five-protein mixture). Data show that the herein disclosed DiGEP strategy was able to detect endogenous phosphorylated proteins labeled with one of our imaging reagents in a whole cell extract of E. coli BL21 strain (FIG. 3b; Lane 1). Referring to FIG. 3b, the signals were due to protein phosphorylation because all signals disappeared when cell extract was treated with a generic phosphatase, CIAP (Lane 2). Moreover, still referring to FIG. 3b, phosphoproteins β-casein and ovalbumin were clearly detected (Lane 3) when spiking the five-protein mixture into CIAP-treated E.

*coli* cell extract before labeling. Protein gel staining with Sypro Ruby indicates equal cell extract loading (FIG. 3a).

Figure 2:
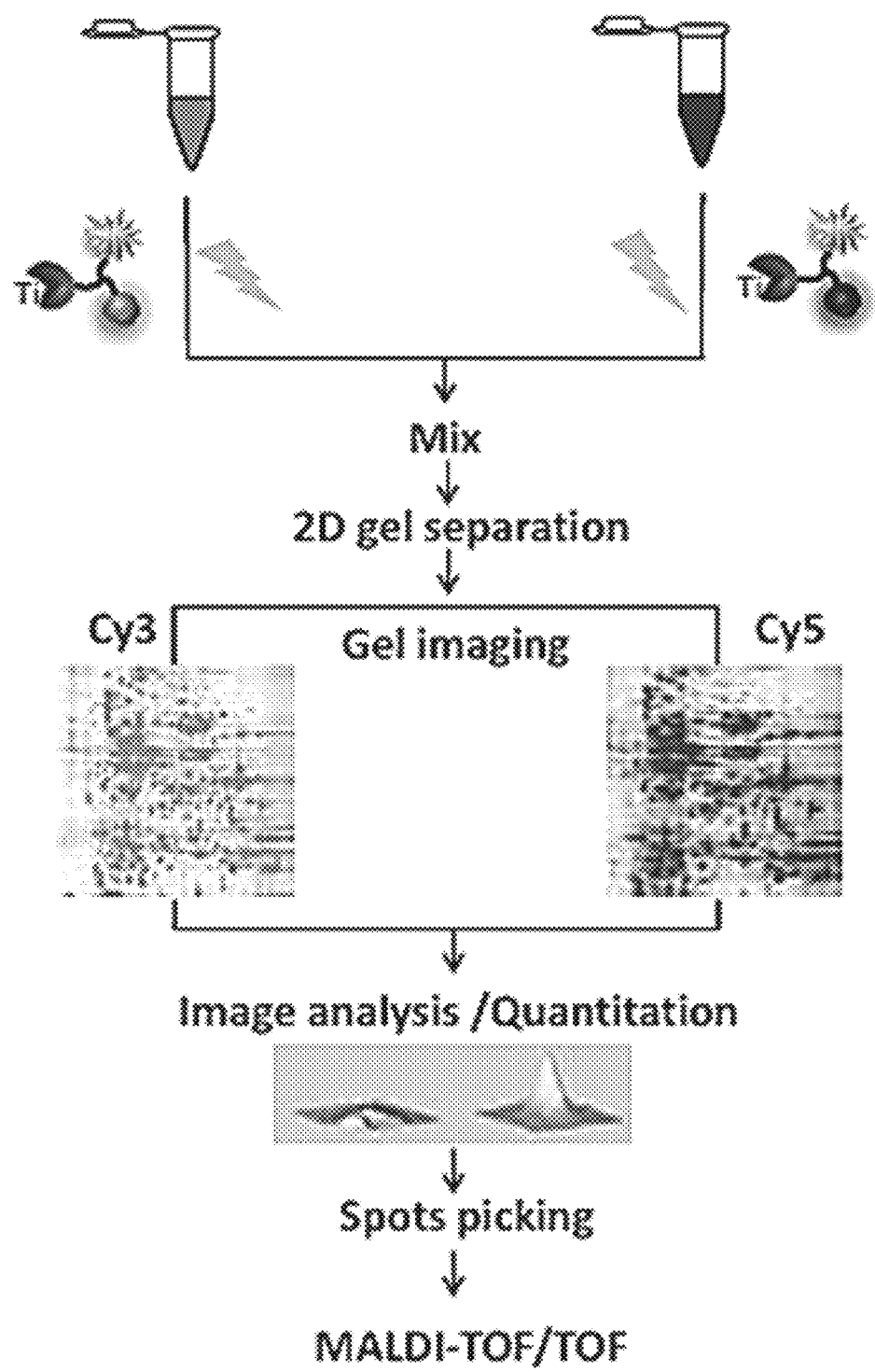
FIG. 2 is a schematic illustration of the herein disclosed DiGEP strategy for phosphoproteomic analyses.

Another embodiment of the present disclosure involves development of DiGEP family products for high sensitivity and specificity. Although for the purposes of this embodiment we mainly focus on the imaging reagents as shown in FIG. 1, alternative embodiments of the present disclosure focus on improving the sensitivity and specifity of DiGEP. Two approaches will be exemplary of these alternative embodiments: one is to substitute Cy3 and Cy5 with more sensitive and more robust fluorophores. For example, infrared (IR) and near-infrared (NIR) fluorescent dyes (e.g., IRDye 800 and 680 series from LI-COR) delivers enhanced sensitivity due to low background autofluorescence in the near-infrared region and, therefore, higher signal to noise ratios. These fluorescent dyes have similar size, the same charge, but distinctive wavelength. Another approach is to introduce more than one Ti (IV) ion and fluorophore per each molecule to improve the binding affinity to phosphoproteins and amplify the signal. Current synthesis of the imaging reagents starts from orthogonally protected lysine and uses solid phase to add different functional groups step by step. In yet another embodiment, the synthesis can be modified to extend the reaction to include more than one Ti (IV) ions and more than one fluorophore groups while maintaining relatively small size.

Herein we focus on improving the sensitivity and specificity of DiGEP. One issue to address is whether photoreactive linker will crosslink any protein in close distance, in particular those proteins interacting with phosphoproteins and therefore introducing false positives. Surprisingly, preliminary data examplified in FIGS. 3a and 3b indicates it is not the case. We reason that due to the use of high concentration of selectivity enhancers, such as glycolic acid, lactic acid, or dihydroxybenzoic acid (DHB), protein-protein interactions are disrupted and therefore unphosphorylated proteins are not crosslinked by the imaging reagents. We evaluated different biological systems to optimize the labeling condition and minimize crosslinking of unphosphorylated proteins. On the other hand, the labeling solution containing an organic acid as selectivity enhancer can lead to protein precipitation. With appropriate buffer (such as 100 mM HEPES), no precipitation was observed in simple protein mixtures or mixtures as complex as a whole cell extract. We carefully examined different biological systems to make sure the labeling condition does not lead to detectable protein precipitation.

Difference Gel Electrophoresis of Phosphoproteomes

DIGE allows for accurate quantification of proteomes with statistical confidence while controlling for non-biological variation, and also increases the dynamic range and sensitivity of traditional 2D PAGE. The herein disclosed DiGEP uses a similar concept to quantify phosphoproteomes with high confidence. With inclusion of an appropriate internal standard typically formed from equal amounts of every sample in an experiment, DiGEP technology also allows for repetitive measurements and multi-variable analyses to be quantitatively analyzed in one coordinated experiment, yielding data about significant changes in protein phosphorylation related to many disease states. Once the herein disclosed technique is optimized as described herein by focusing on quantitation and targeted analyses of complex biological samples, this novel approach provides an important tool in clinical proteomics and the study of the mechanism of disease, investigating diagnostic biomarkers and pinpointing novel therapeutic targets.

Figures 4A, 4B:
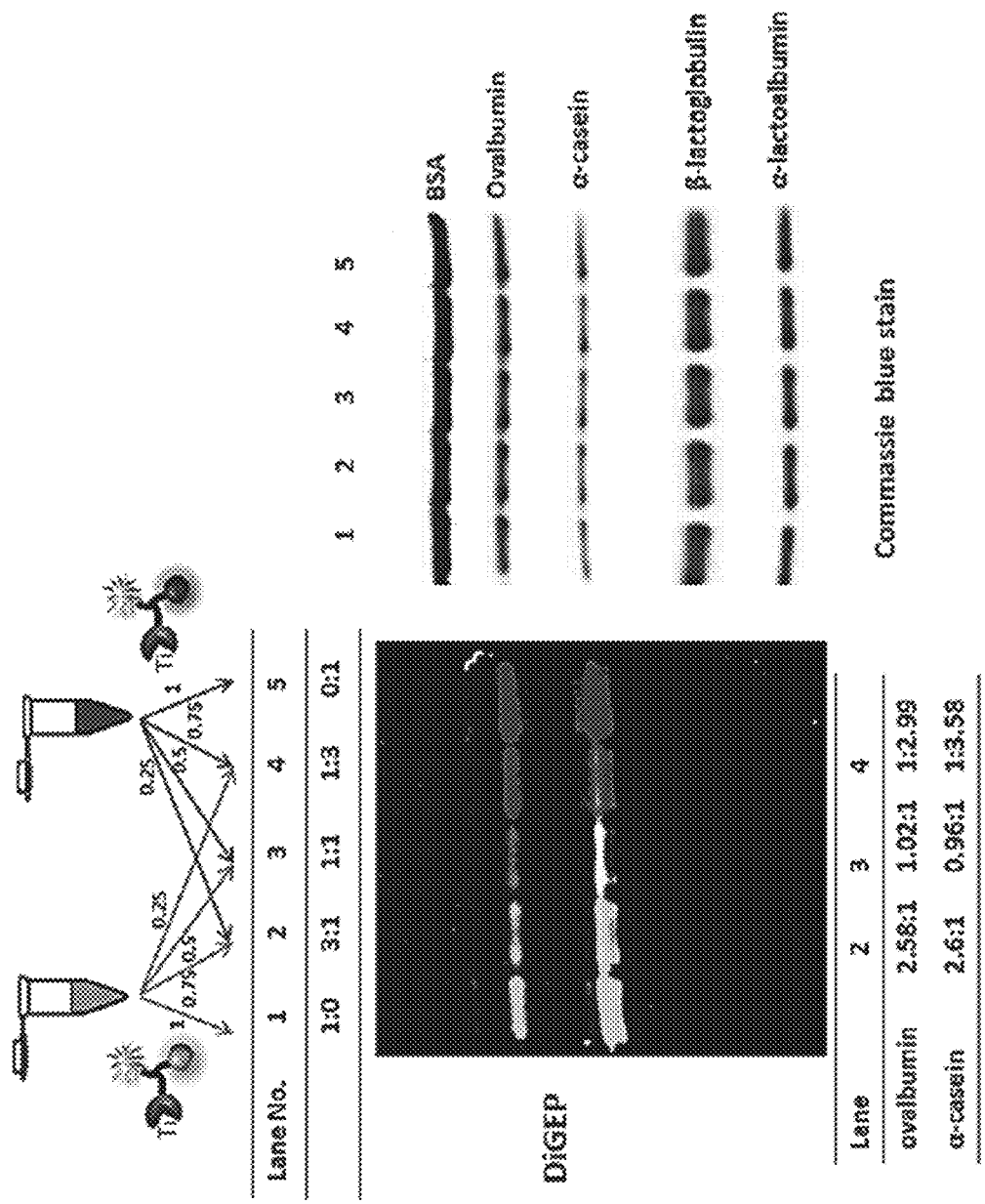

Quantitative Ability of DiGEP:

An important feature of DiGEP is its ability to differentially visualize phosphoproteins within a complex mixture in the gel. We use simple protein mixtures containing phosphoproteins and non-phosphoproteins and complex samples such as whole cell extracts to evaluate its quantitative nature and dynamic range. Data show a five-protein mixture (BSA, β-lactoglobulin and α-lactoalbumin are non-phosphorylated proteins; α-casein and ovalbumin are phosphorylated proteins) in different ratios was labeled with the imaging reagents bearing either Cy3 or Cy5. Cy3- and Cy5-labeled samples were pooled for SDS-PAGE analysis. As shown in FIGS. 4a and 4b (which depict quantitative visualization of phosphoproteins in five-protein mixture; proteins in different portions were labeled and then mixed for DiGEP analysis; FIG. 4a shows the overlap of Cy3 and Cy5 excitation scan; referring to FIG. 4b, the proteins were also stained by Coomassie blue; referring to FIG. 4a, the original ratio is shown at the top of the image and the measured ratio is shown below the image), Coomassie Blue staining indicates labeling with Cy3 and Cy5 did not change the mobility in gel electrophoresis. Only the two phosphoproteins, α-casein and ovalbumin, were visible in fluorescence detection, again showing good selectivity. Quantitative analysis of images under two different fluorescence wavelengths revealed the ratio of two protein samples close to the theoretical value. Linearity and accuracy of DiGEP quantitation are also further examined with more detail.

Fast Identification of Relevant Phosphoproteins in DiGEP:

DiGEP allows us to first visualize the phosphoproteins in the gel and then choose those showing distinctive difference in different states for mass spectrometric analysis. The spot can be picked manually or by instrument and subjected to in-gel digestion. To confidently identify phosphorylated proteins, the detection of actual phosphopeptides is typically required. Due to the relatively low stoichiometric nature and ionization efficiency of phosphopeptides in mass spectrometric analysis, an efficient enrichment step is beneficial in phosphoproteomic studies. In an embodiment, we apply a novel homogenous isolation method based on polymer-based metal ion affinity capture (PolyMAC). PolyMAC modified with Ti (IV) ion has proven to be extremely efficient to enrich phosphopeptides with high specificity in different biological samples.

Although different types of ionization and mass spectrometers can be used to sequence peptides, MALDI-TOF/TOF is typically used for peptide sequencing after in-gel digestion due to its high throughput and speed. In an example, we use the ABI 4800 MALDI-TOF/TOF for mass spec analyses. With its high throughput, such a phosphoproteomic analysis can be expected to be completed within a day. In contrast, a typical phosphoproteomic experiment based on shot-gun proteomics may take multiple days to acquire the data and weeks for data analysis before identifying the phosphoproteins that are relevant to the specific signaling event.

DiGEP Analyses of Signaling Events in Response to Kinase Inhibition:

We optimize the whole DiGEP procedure and evaluate its sensitivity and specificity by analyzing phophoproteomes of cancer cells in response to the treatment by kinase inhibition. We use the human myelogenous leukemia line, K562, as a model. K562 cells are BCR-ABL active and are sensitive to several kinase inhibitors such as Imatinib, Dasatinib and Bosutinib. These inhibitors have been characterized to inhibit specific kinase ABL and a few other tyrosine kinases such as Src family kinases. Extensive studies have been conducted with the cells. Therefore, it is a relatively complex system and is well-suited for DiGEP optimization. As outlined in FIG. 2, K562 cells are treated with one of the inhibitors (as a control, K562 cells are treated with DMSO solvent only). The same amount of whole cell extracts are incubated with Cy3- or Cy5-imaging reagents, respectively. After removing excess imaging reagents using gel filtration, protein samples are subjected to UV crosslinking, combined, and loaded onto IEF and SDS PAGE gels for 2D separation. We use imaging software to identify spots that show adequate difference in fluorescence intensity, which is subjected to in-gel digestion and PolyMAC enrichment of phosphopeptides for mass spectrometric identification. For Imatinib treatment, we can identify phosphoproteins related to ABL inhibition, while Dasatinib or Bosutinib treatment lead to identification of phophoproteins related to ABL and Src family kinases.

The herein disclosed DiGEP strategy offers the most benefit while profiling phosphoprotein networks involving multiple samples, such as various kinase inhibitor screening. When used in conjunction with well-considered experimental design, the result is the accurate measurement of differential protein phosphorylation from across a set of samples. We can adopt a similar approach as typical DIGE by employing the third fluorophore Cy2 to label the pooled mixture that includes equal amounts of each of the samples in the study, and acts as an internal standard. The internal standard ensures that all proteins present in the samples are represented, assisting both inter- and intra-gel matching. Changes in spot volumes due to gel-specific variations, such as sample entry, electrophoresis in either the first dimension immobilized pH gradient (IPG) strip or second dimension SDS-PAGE gel, are the same for each sample within a gel, facilitating accurate measurements of phosphorylation.

Those skilled in the art will recognize that numerous modifications can be made to the specific implementations described above. The implementations should not be limited to the particular limitations described. Other implementations may be possible.

The invention claimed is:

1. A trifunctional imaging reagent, comprising:
a core linkage having the structure of

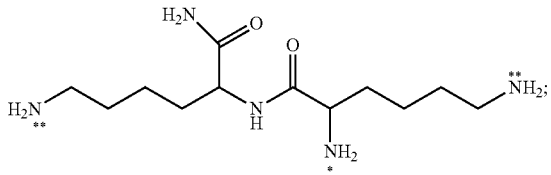 [SMILES: NCCCCC(N)C(=O)NC(CCCCN)C(N)=O]

a photo-reactive group comprising diazirine;
a metal chelating group comprising a phosphate group, wherein the phosphate group has binding specifity to metal ions selected from the group consisting of Ti (VI), Zr (VI), Fe (III) and Ga (III); and
a fluorophore selected from the group consisting of Cy3, Cy5, infrared IR Dye 800 and infrared IR Dye 600, wherein the core linkage is covalently connected to the photo-reactive group, the metal chelating group and the fluorophore through an amide bond, wherein * represents the point of attachment of the fluorophore, ** represents the point of attachment of photo-reactive group and metal chelating group respectively, and wherein the metal chelating group is not linked to the core linkage through phosphate group, and photo-reactive group is not linked to the core linkage through diazirine group.

2. A kit comprising a phosphoprotein differentiating imaging reagent, the phosphoprotein differentiating imaging agent comprises a pair of the trifunctional imaging reagents of claim 1, wherein both of the trifunctional imaging reagent in the pair are bound to the same metal ion from the selection and wherein the fluorophore in each of the trifunctional imaging reagent in the pair are selected from the selection such that the fluorophore are of different color.

* * * * *